(12) United States Patent
Mizutani et al.

(10) Patent No.: US 6,592,563 B2
(45) Date of Patent: Jul. 15, 2003

(54) ABSORBENT ARTICLE HAVING LEAKAGE PREVENTING SIDEWALLS ON LATITUDINAL SIDES OF THE LIQUID RECEIVING SIDE

(75) Inventors: Satoshi Mizutani, Kagawa (JP); Tatsuya Tamura, Kagawa (JP); Yuuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 30 days.

(21) Appl. No.: 09/803,795

(22) Filed: Mar. 12, 2001

(65) Prior Publication Data

US 2001/0021837 A1 Sep. 13, 2001

(30) Foreign Application Priority Data

Mar. 13, 2000 (JP) ........................................ 2000-068297

(51) Int. Cl.$^7$ ................................................ A61F 13/15
(52) U.S. Cl. ................................................ 604/385.28
(58) Field of Search ........................ 604/385.04, 385.01, 604/385.24, 385.28

(56) References Cited

U.S. PATENT DOCUMENTS

| 4,695,278 A | * | 9/1987 | Lawson | ................. 604/385.27 |
| 5,085,654 A | | 2/1992 | Buell | |
| 5,674,213 A | | 10/1997 | Sauer | |
| 6,280,428 B1 | * | 8/2001 | Lash et al. | ............. 604/385.04 |
| 6,328,723 B1 | * | 12/2001 | Burns, Jr. et al. | ........ 604/385.22 |
| 6,358,233 B1 | * | 3/2002 | Taylor | ................... 604/385.04 |
| 6,458,113 B2 | * | 10/2002 | Kashiwagi | ............. 604/385.16 |
| 6,475,200 B2 | * | 11/2002 | Mizutani et al. | ........ 604/385.01 |
| 2001/0021834 A1 | * | 9/2001 | Yoshimasa | ............. 604/385.01 |
| 2001/0021839 A1 | * | 9/2001 | Kashiwagi | ................... 604/400 |

FOREIGN PATENT DOCUMENTS

| EP | 0626160 A1 | 11/1994 |
| EP | 0745367 A2 | 12/1996 |
| EP | 0788874 A1 | 8/1997 |
| JP | 08-215244 | 8/1996 |
| WO | WO 96/23471 | 8/1996 |
| WO | WO 97/09017 | 3/1997 |

* cited by examiner

Primary Examiner—Weilun Lo
Assistant Examiner—Michael Bogart
(74) Attorney, Agent, or Firm—Darby & Darby

(57) ABSTRACT

There is disclosed an absorbent article including: a main body of a support sheet, a liquid absorbing layer and a liquid-permeable sheet; and leakage preventing side walls provided on two sides of the main body and extending in the longitudinal direction, to have root ends jointed to the surface of the liquid receiving side and to have free ends positioned apart from the surface of the liquid receiving side. Each leakage preventing side wall is formed of at least one side wall sheet to have an inner sheet portion facing the widthwise inner side of the absorbent article and an outer sheet portion facing the widthwise outer side of the absorbent article. The inner sheet portion are provided with holes leading to the inside of the inner and outer sheet portions.

1 Claim, 7 Drawing Sheets

ABSORBENT ARTICLE HAVING LEAKAGE PREVENTING SIDEWALLS ON LATITUDINAL SIDES OF THE LIQUID RECEIVING SIDE

BACKGROUND OF THE INVENTION

1. Field of the Invention

The present invention relates mainly to an absorbent article for absorbing and retaining a liquid waste such as menstrual blood and, more particularly, to an absorbent article having leakage preventing side walls on the two widthwise sides of the liquid receiving side.

2. Related Art

In the prior art, there have been a variety of absorbent articles including a sanitary napkin, a urine absorbing pad and a disposable diaper. These absorbent articles are demanded, when worn, for absorbing the liquid waste reliably in liquid absorbing layers so that the liquid waste may not leak to the outside of the absorbent articles. For this purpose, there is an absorbent article which is provided on the surface of the liquid receiving side with leakage preventing side walls extending longitudinally on the two widthwise sides.

In the general structure of the leakage preventing side walls of the prior art, a longitudinally extending hydrophobic sheet is jointed to the top sheet of the absorbent article, and an elastic member extending longitudinally of the absorbent article is jointed to the hydrophobic sheet. By the elastic shrinking force in the longitudinal direction of the elastic member, a curving force in the longitudinal direction is applied to the absorbent article, and the leakage preventing side walls are raised to the liquid receiving side of the absorbent article so that the menstrual blood or the like may be prevented from leaking sideways.

In Japanese Patent Laid-Open No.215244/1996, for example, there is disclosed an absorbent article, the leakage preventing side walls of which are made of a synthetic resin film formed into a non-planar shape. In this absorbent article, the leakage preventing side walls thus subjected to the non-planar treatment to form longitudinal wrinkles are brought into facial contact with the skin of a wearer.

However, this absorbent article of the prior art has been frequently unable to guide the menstrual blood or the like, as having blotted the surfaces of the leakage preventing side walls, reliably to the side of the liquid absorbing layer so that the wearer is made to feel a physical disorder with the menstrual blood residing on the leakage preventing side walls and to cause the sideway leakage. In the structure, as disclosed in Japanese Patent Laid-Open No.215244/1996, the wrinkled leakage preventing side walls come into facial contact with the skin of the wearer, so that the menstrual blood or the like is liable to stay between the wrinkles although the contacts between the skin and the leakage preventing side walls are satisfactory. In addition, the leakage preventing side walls with the menstrual blood residing thereon come into facial contact with the wearer to intensify the uncomfortable feel at the wearing time.

SUMMARY OF THE INVENTION

The invention has an object to provide an absorbent article which is enabled to improve the wearing feel and to prevent the sideway leakage effectively by making it easy to guide the blotting liquid to the side of the liquid absorbing layer thereby to suppress the stay of the menstrual blood or the like on the leakage preventing side walls.

According to an aspect of the invention, there is provided an absorbent article comprising:

a main body including a support sheet, a liquid absorbing layer laid on the support sheet, and a liquid-permeable sheet provided on a liquid receiving side of the main body and covering the liquid absorbing layer; and leakage preventing side walls provided on two sides of the main body lying opposite one another in the widthwise direction and extending in the longitudinal direction, to have root ends jointed to the surface of the liquid receiving side and to have free ends positioned apart from the surface of the liquid receiving side, wherein each the leakage preventing side walls is formed of at least one side wall sheet to have an inner sheet portion facing the widthwise inner side of the absorbent article and an outer sheet portion facing the widthwise outer side of the absorbent article, and wherein the inner sheet portion are provided with holes leading to the inside of the inner and outer sheet portions.

In the absorbent article of the invention, the menstrual blood, urine or the like infiltrates, when it blots the surface of the side wall sheet forming the leakage preventing side wall, into the space between the inner and outer sheet portions from the holes so that it is guided as it is to the root end through the space between the inner and outer sheet portions. Therefore, the liquid having blotted the side wall sheet does not reside in the side wall sheet but can prevent the sideway leakage effectively. Moreover, in the case where the leakage preventing side wall is inclined with its free end directed toward the widthwise outer side so that the leakage preventing side wall comes into facial contact with the skin of the wearer, the liquid hardly stays on the surface of the side wall sheet to contact with the skin so that the absorbent article is reluctant to give an uncomfortable feel to the wearer.

For example, it is preferable that the inner sheet portion is corrugated and that the holes are formed in at least the ridges of the corrugations.

With this construction, the liquid can enter the space between the inner and outer sheet portions of the leakage preventing side wall from the holes. Moreover, when the liquid enters the space between the confronting inner and outer sheet portions from the holes, it is retained on the inner faces of the ridges of the side wall sheet or guided to the root end along the inner faces of the ridges, so that the liquid is reluctant to stay on the surface of the side wall sheet facing the skin of the wearer.

The side wall sheet may be formed of a nonwoven fabric which is made of hydrophobic fibers or made hydrophobic (i.e., subjected to a hydrophobic treatment), or a hydrophobic resin sheet. The side wall sheet may be given later natural corrugations by the shrinking force of an elastic member or the like, without providing corrugations in advance. However, the preferable side wall sheet is corrugated in the following manner.

For example, it is preferable that the inner sheet portion is provided at least in its portion with: the corrugations of which the ridges and valleys are extended from the root end to the free end and arranged regularly in the longitudinal direction; and a flat portion extending in a direction of crossing the ridges and valleys of the corrugations, and that the holes are formed in the boundary portion between the ridges of the corrugations and the flat portion.

With the corrugations being thus formed to extend at their ridges and valleys from the root end to the free end and with the holes being formed in the end portions of the ridges, the menstrual blood or the like infiltrates into those ridges from the holes and is guided to the root end along the inner faces of the ridges.

Here, the term "flat portion" means a smooth surface portion where the side wall sheet is never corrugated or is corrugated lower than the aforementioned corrugations.

For example, the holes may be formed by rupturing the side wall sheet when the corrugations and the flat portion are shaped. If the holes are formed by the rupturing method, they can be formed at the same step as that of corrugating the side wall sheet.

The flat portion may extend in the longitudinal direction, and an elastic member for exhibiting an elastic shrinking force in the longitudinal direction may be jointed to the flat portion between the inner and outer sheet portions.

For example, when the inner and outer sheet portions are formed by folding back the side wall sheet, the flat portion may be formed at the folded-back portion of the side wall sheet forming the free end of the leakage preventing side wall. In an alternative, the flat portion may be formed midway between the root end and the free end of the leakage preventing side wall. In another alternative, the flat portion may be formed midway between the root end and the free end of the leakage preventing side wall, and the leakage preventing side wall may be so bent at the flat portion that its portion extending from the bent portion to the free end may be directed to the widthwise outer side.

Moreover, it is preferable that the holes are formed in or in the vicinity of the root end of the leakage preventing side wall. With the holes being formed on the side of the root end of the leakage preventing side wall, the menstrual blood or the like, as guided into the space between the inner and outer sheet portions, is then guided from the holes on the root end side to the liquid-permeable sheet and further to the liquid absorbing layer.

In order to release the liquid, which has entered the space between the inner and outer sheet portions, reliably from the root end side to the liquid-permeable sheet, it is preferable that the leakage preventing side walls are jointed at the root ends either onto two side end portions of the liquid-permeable sheet, as extending outwardly of the liquid absorbing layer in the widthwise direction, or onto a central portion of the liquid-permeable sheet, as positioned between the two side end portions and over the liquid absorbing layer.

If the inner and outer sheet portions are made water-repellent at their inner faces confronting each other, the liquid having entered the space between the inner and outer sheet portions is promptly guided to the root end side.

DESCRIPTION OF THE PREFERRED EMBODIMENTS

Figure 1:
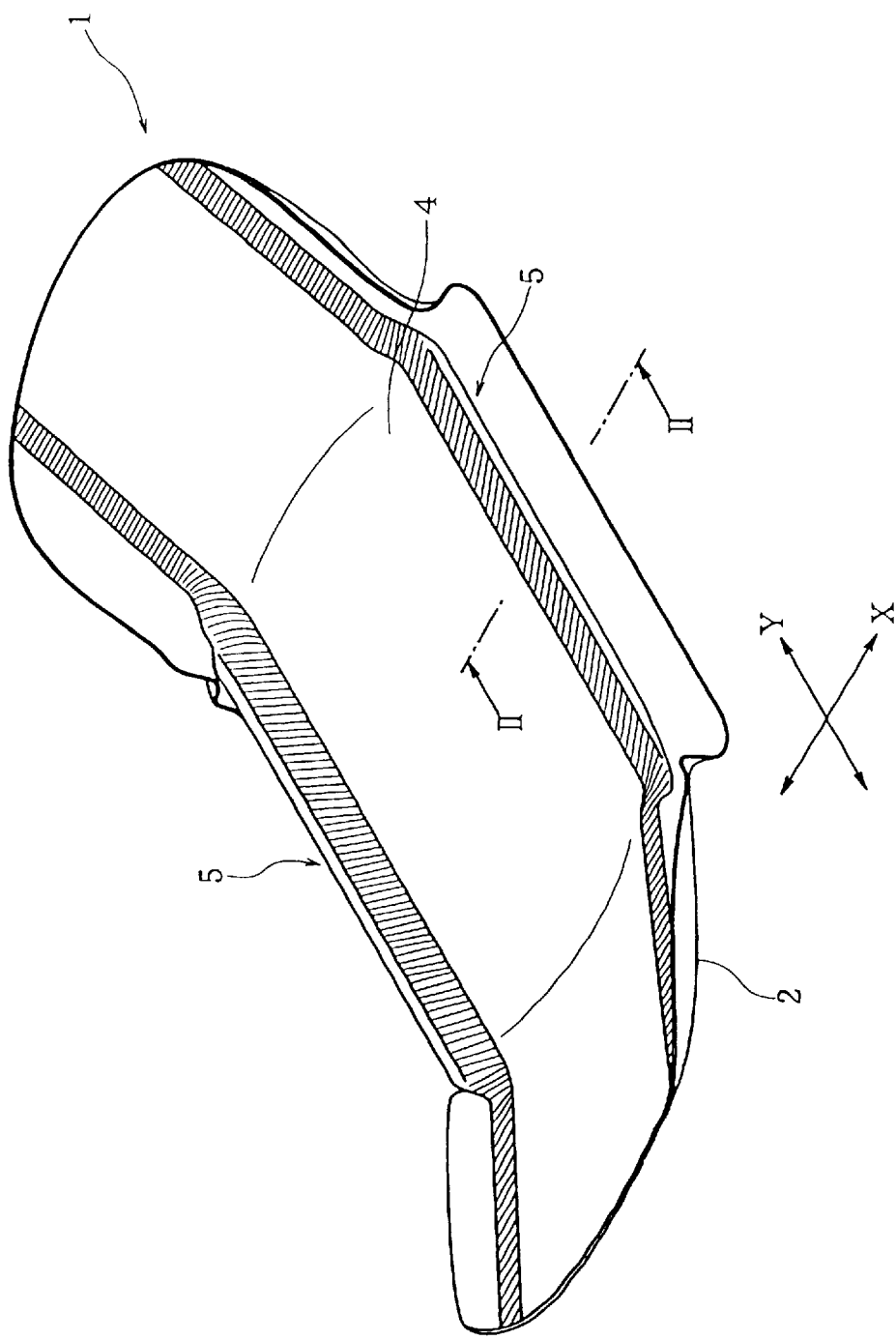
FIG. 1 is a perspective view showing a sanitary napkin as an absorbent article according to a first embodiment of the invention.
Figure 2:
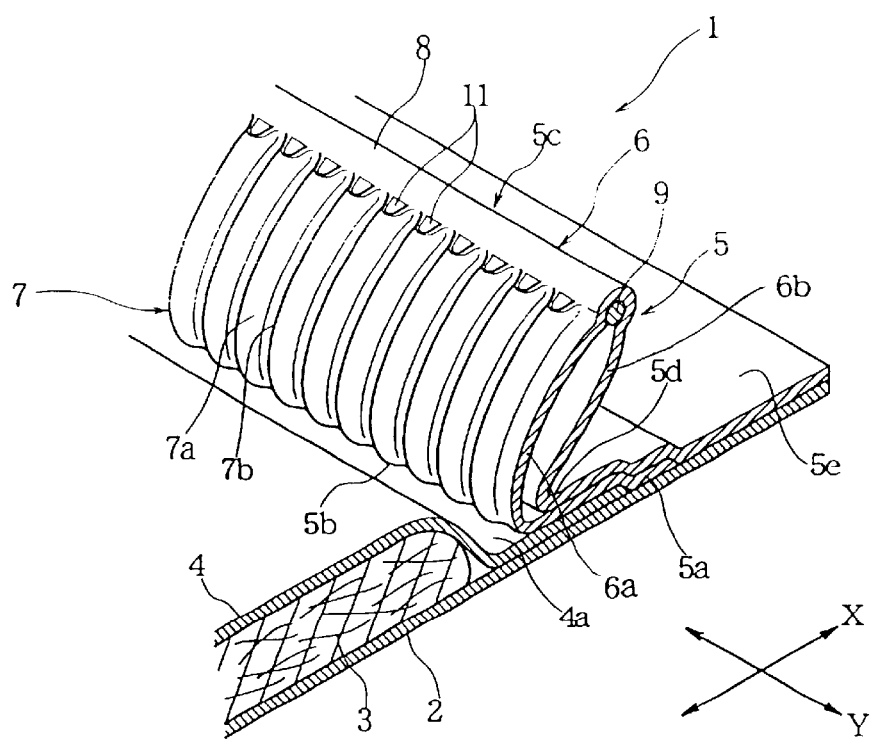
FIG. 2 is a perspective view showing a portion of the sanitary napkin shown in FIG. 1 and including a section taken along line II—II.
Figure 5:
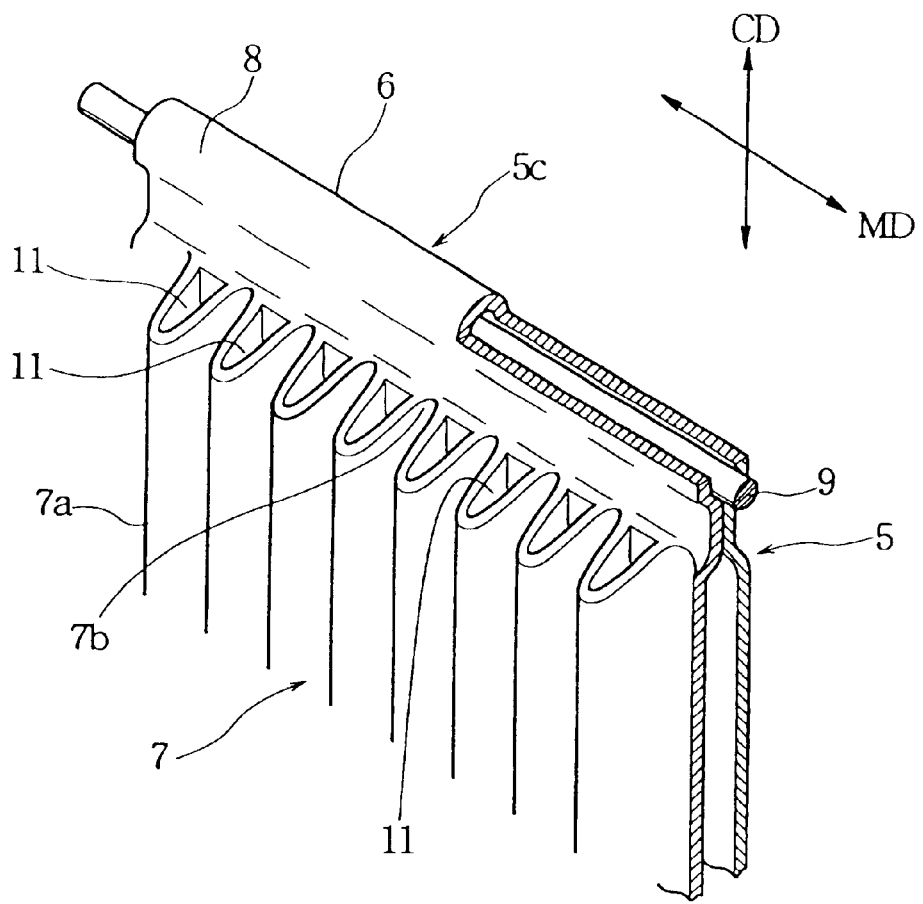
FIG. 5 is an enlarged perspective view showing a structure of a leakage preventing side wall shown in FIG. 2.

The invention will be described with reference to the accompanying drawings. FIG. 1 is a perspective view showing a sanitary napkin as an absorbent article according to a first embodiment of the invention and taken from a liquid receiving side; FIG. 2 is a perspective view showing a portion and including a section taken along line II—II of FIG. 1; and FIG. 5 is an enlarged view of a portion showing a free end of a leakage preventing side wall shown in FIG. 2.

A sanitary napkin 1, as shown in FIGS. 1 and 2, is constructed to have a main body including: a support sheet 2 for confronting an external wear such as an underwear; a liquid absorbing layer 3 positioned on the side of the wearer for absorbing the liquid waste; and a liquid-permeable sheet 4 for covering the surface of the liquid receiving side of the liquid absorbing layer 3. Side end portions 4a of the liquid-permeable sheet 4 lying opposite one another in the widthwise direction (or a direction X) are jointed onto the surface of the support sheet 2 on two sides of the liquid absorbing layer 3.

On the two side portions of the sanitary napkin 1 lying opposite one another in the widthwise direction (or the direction X), there are provided a pair of leakage preventing side walls 5 and 5 which extend in the longitudinal direction (or a direction Y). In this embodiment, the individual leakage preventing side walls 5 and 5 are made of one side wall sheet 6.

The side wall sheet 6 is, for example, made of a hydrophobic nonwoven fabric. This sidewall sheet 6 is jointed at its one end portion 5a onto the support sheet 2 and the side end portion 4a of the liquid-permeable sheet 4. The side wall sheet 6 is extended away from the support sheet 2 to form one root end 5b of the side wall 5 on the side end portion 4a of the liquid-permeable sheet 4 and is then folded back to form a free end 5c of the side wall 5. Moreover, the side wall sheet 6 is returned to the support sheet 2 and is so jointed at its other end portion 5e to the upper face of the support sheet 2 that another root end 5d of the side wall 5 is formed and jointed onto the side end portion 4a of the liquid-permeable sheet 4. Therefore, the leakage preventing side wall 5 has a double structure in which the two folded portions (or inner and outer sheet portions 6a and 6b) of the side wall sheet 6 are overlaid in the widthwise direction (or the direction X).

The side wall sheet 6 is formed with corrugations 7. These corrugations 7 have ridges 7a and valleys 7b repeated in the longitudinal direction (or the direction Y). The ridges 7a and the valleys 7b are individually extended in the direction from the root ends 5b and 5d to the free end 5c of the leakage preventing side wall 5.

As shown in FIGS. 2 and 5, moreover, the side wall sheet 6 is formed with a flat portion (or smooth surface portion) 8. The side wall sheet 6 is folded back at the flat portion 8 to form the free end 5c. To this free end 5c, moreover, there is internally jointed an elastic member 9. Here, this elastic member 9 may be arranged at the portion other than the free end 5c, that is, between the root ends 5b and 5d and the free end 5c of the leakage preventing side wall 5.

The side wall sheet 6 having the corrugations 7 exhibits by itself an elastic shrinking force in the longitudinal direction (or the direction Y). In addition, the elastic member 9 also exhibits an elastic shrinking force in the longitudinal direction (or the direction Y). At the two end portions of the sanitary napkin 1 lying opposite one another in the longitudinal direction (or the direction Y), the leakage preventing side walls 5 are jointed to the surface of the liquid receiving side of the main body while falling down outwardly in the widthwise direction. By the elastic shrinking forces in the direction Y, therefore, the sanitary napkin 1 is so curved that its liquid receiving side is recessed in the longitudinal direction (or the direction Y), as shown in FIG. 1, and the leakage preventing side walls 5 are raised at their free ends 5c apart from the support sheet 2. Here in the embodiment shown in FIG. 2, the leakage preventing side walls 5 and 5 are so obliquely raised that the free ends 5c are directed outwardly in the widthwise direction with respect to the root ends 5b and 5d.

As shown in FIGS. 2 and 5, moreover, in the inner sheet portion 6a of the side wall sheet 6, there are formed holes (or openings) 11 which are positioned at the boundary portion between the corrugations 7 and the flat portion 8 and at the end portions of the ridges of the corrugations 7. The menstrual blood is infiltrated through the liquid-permeable sheet 4 and absorbed by the liquid absorbing layer 3. When fed to the inner sheet portion 6a of the side wall sheet 6 constructing the leakage preventing side wall 5, the menstrual blood is guided on the surface of the side wall sheet 6 along the valleys 7b of the corrugations 7 onto the liquid-permeable sheet 4. On the other hand, the menstrual blood, as might otherwise stay on the surface of the side wall sheet 6, flows from the holes 11 into the space between the inner and outer sheet portions 6a and 6b of the side wall sheet 6 constructing the leakage preventing side wall 5 and then migrates along the inner surfaces of the corrugations 7 to the root end 5b until it is fed to the liquid-permeable sheet 4.

Here, it is also preferred that the inner sheet portion 6a of the side wall sheet 6 is formed with a flat portion in or in the vicinity of the root end 5b, and that holes similar to those on the side of the free end 5c are formed on the side of the root end 5b. The menstrual blood flows to the root end 5b between the inner and outer sheet portions 6a and 6b and is fed through the holes opened on the side of the root end 5b to the liquid-permeable sheet 4, from which the blood is absorbed through the liquid-permeable sheet 4 by the liquid absorbing layer 3.

Here in the embodiment shown in FIGS. 1 and 2, the leakage preventing side wall 5 is jointed on the side end portion 4a, as extended outwardly of the liquid absorbing layer 3 in the widthwise direction, of the liquid-permeable sheet 4. As described hereinbefore, therefore, the menstrual blood having migrated through the space between the inner and outer sheet portions 6a and 6b is fed to the liquid-permeable sheet 4 so that it is easily led to the liquid absorbing layer 3. In an alternative, the leakage preventing side walls 5 may be given the structure in which they rise from the central portion, as located between the two side end portions 4a and 4a and covering the liquid absorbing layer 3, of the liquid-permeable sheet 4. With such a structure, also, the menstrual blood having migrated through the space between the inner and outer sheet portions 6a and 6b can be easily absorbed by the liquid absorbing layer 3.

Figure 6:
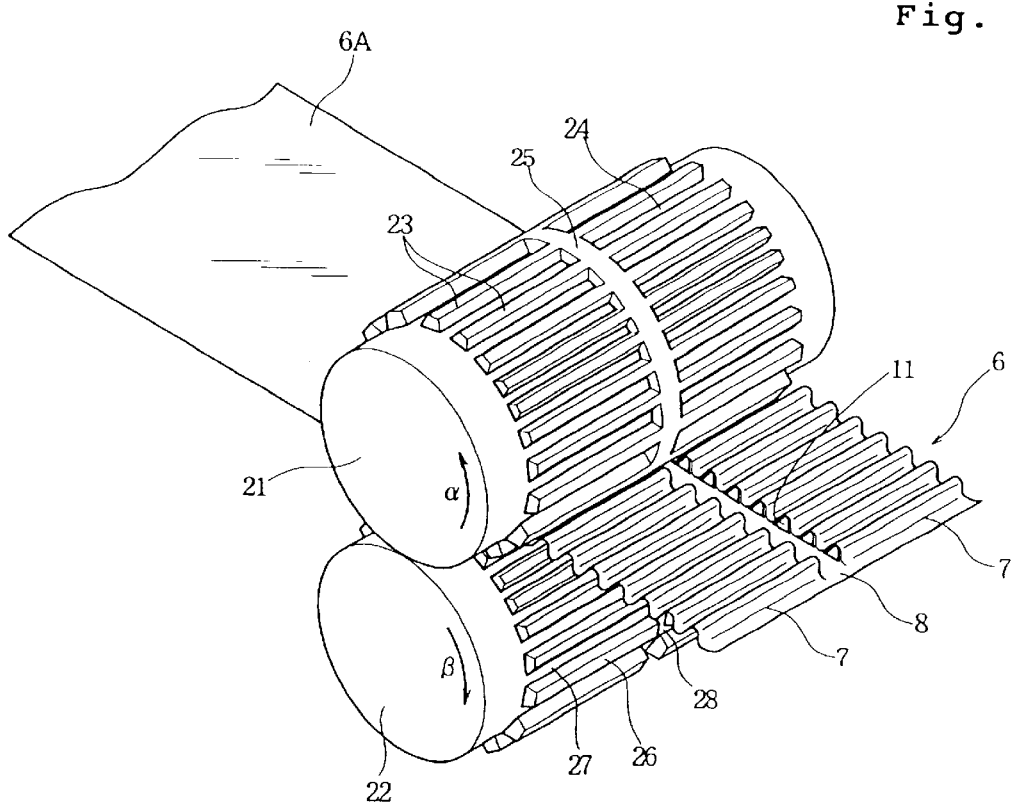
FIG. 6 is a perspective view of shaping rolls for forming a side wall sheet.

FIG. 6 is a view for explaining a heat-pressing step of forming the corrugations 7 and the flat portion 8 on the side wall sheet 6 and forming the holes 11 in the boundary portion between the corrugations 7 and the flat portion 8 at the same time.

At this heat-pressing step, a nonwoven fabric such as a melt-blown nonwoven fabric formed of or containing thermoplastic fibers is heat-pressed by clamping it between shaping rolls 21 and 22. These shaping rolls 21 and 22 are turned in directions α and β while meshing with each other.

Figure 7A:
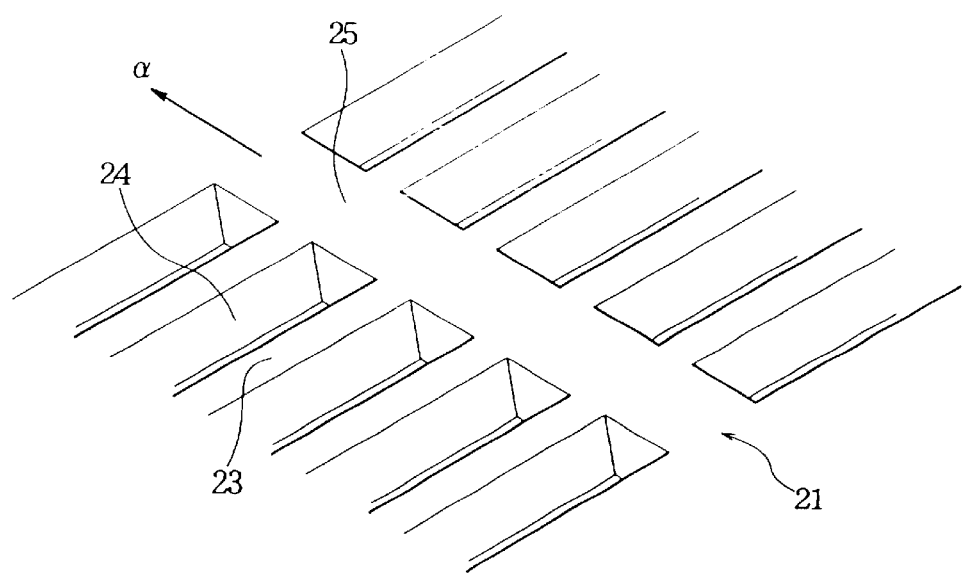
FIGS. 7A and 7B are developed perspective views of the shaping faces of the shaping rolls shown in FIG. 6.

The shaping roll 21 has a shaping face formed on its surface. FIG. 7A develops and shows the top plan view of the shaping face of the surface of the shaping roll 21. In the shaping face of the shaping roll 21, there are stripe embossed shaping ribs 23 and grooves 24 which are extended in the axial direction of the roll and repeated at a constant pitch in the turning direction (or the direction α). At the axial central portion of the shaping roll 21, there is formed a bulging circumference 25 which continues to the upper faces of the shaping ribs 23 and is extended continuously in the turning direction (or the direction α).

Figure 7B:
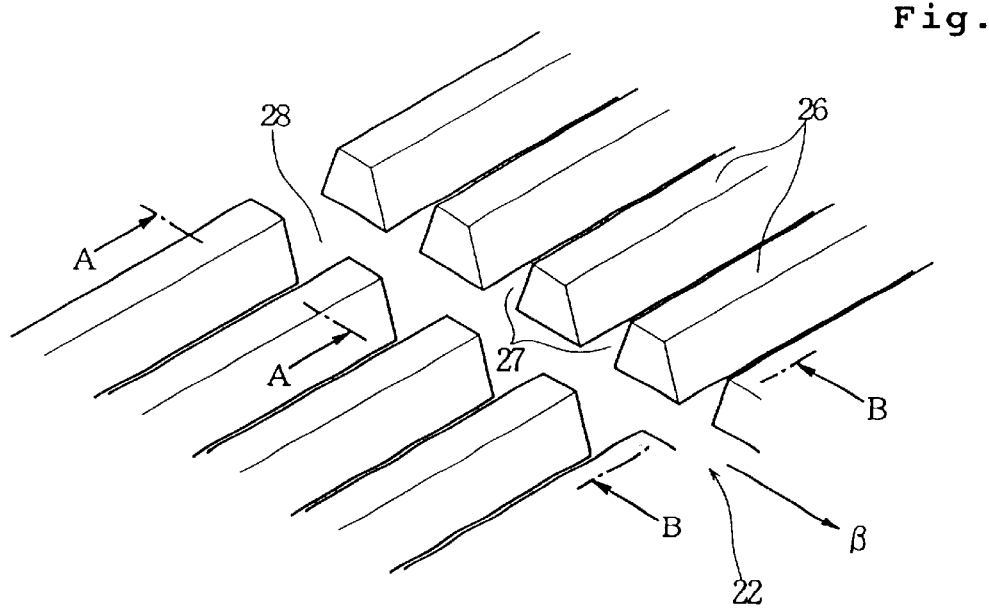

FIG. 7B develops and shows the shaping face of the surface of the other shaping roll 22. In the shaping face of the surface of the shaping roll 22, there are stripe embossed shaping ribs 26 and grooves 27 which are extended in the axial direction of the roll and repeated at a constant pitch in the turning direction (or the direction β). At the axial central portion of the shaping roll 22, there is formed a recessed circumference 28 which continues to the bottom portions of the grooves 27 and is extended continuously in the turning direction (or the direction β).

When the shaping rolls 21 and 22 come into meshing engagement, the shaping ribs 23 of the shaping roll 21 and the shaping ribs 26 of the shaping roll 22 mesh with each other such that the shaping ribs 23 enter the grooves 27 of the shaping roll 22 whereas the shaping ribs 26 enter the grooves 24 of the shaping roll 21. At this time, the bulging circumference 25 of the shaping roll 21 bites into the recessed circumference 28 of the shaping roll 22.

When a nonwoven fabric 6A is clamped between the shaping rolls 21 and 22 and is let off as the rolls turn, as shown in FIG. 6, the side wall sheet 6 having the corrugations 7, the flat portion 8 and the holes 11 is formed by the shaping faces of the shaping rolls 21 and 22.

The side wall sheet 6 is made of a melt-blown nonwoven fabric, an air-through nonwoven fabric, a spun-bonded nonwoven fabric, a point-bonded nonwoven fabric, an air-laid nonwoven fabric or the like. However, the side wall sheet 6 may be made of a laminate material of the nonwoven fabric and a resin film, or a plastic sheet of a low density.

These are made of a thermoplastic resin, and the nonwoven fabric is exemplified by the PE, PP or PET fibers, or composite synthetic fibers of the core-sheath type of the PE/PP or PE/PET or of the side-by-side type thereof.

Figure 8A:
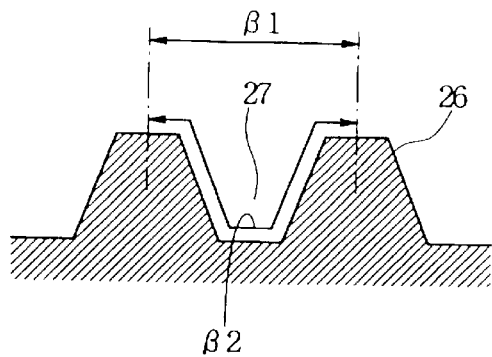
FIGS. 8A and 8B are enlarged sections taken along lines A—A and B—B of FIG. 7B.
Figure 8B:
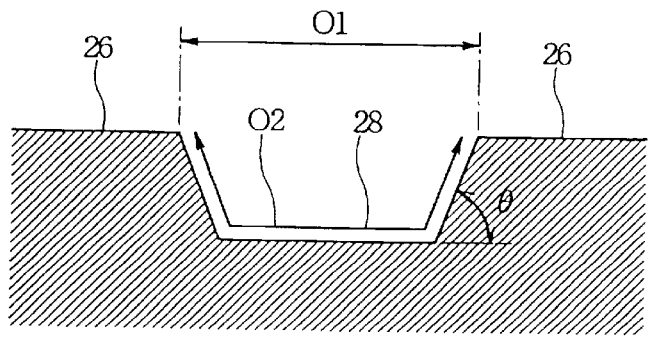

FIG. 8A is a section showing the shaping face of the shaping roll 22 and taken along line A—A of FIG. 7B, and FIG. 8B is a section taken along line B—B of FIG. 7B. The shaping faces of the shaping rolls 21 and 22 are preferably set to a temperature which is lower by 10° C. to 50° C. than the melting point of the thermoplastic resin making the aforementioned sheet.

In FIG. 8A, the array pitch of the shaping ribs 26 in the turning direction (or the direction β) is indicated by β1, and the exceeding size extending through the shaping ribs 26 and the grooves 27 between the array pitch β1 is indicated by β2. When the nonwoven fabric 6A is clamped between the shaping rolls 21 and 22 and let off, the nonwoven fabric 6A is given a shaping distortion of $\{(\beta 2-\beta 1)/\beta 1\}$. This shaping distortion at this time is set to a value smaller than the rupture elongation (or rupture distortion) in the let-off direction of the nonwoven fabric. As a result, the corrugations 7 are formed without rupture on the nonwoven fabric 6A.

If the distance, as taken in the roll axis direction, of the open end of the recessed circumference 28 is indicated by O1 and if the exceeding size, as adding the undulations in the widthwise direction, of the recessed circumference 28 is indicated by O2, as shown in FIG. 8B, the nonwoven fabric 6A is given a shaping distortion of {(O2−O1)/O1} in the roll axis direction (or the widthwise direction of the nonwoven fabric 6A). If this shaping distortion is set larger than the rupture elongation (or the rupture distortion) in the widthwise direction of the nonwoven fabric 6A, the flat portion 8, as extended in the let-off direction, is formed at the widthwise central portion of the nonwoven fabric 6A by the shaping rolls 21 and 22, and the holes 11 are formed by the ruptures of the nonwoven fabric at the boundary portions between the corrugations 7 and the flat portion 8, that is, at the end portions of the ridges of the corrugations 7.

Figure 9:
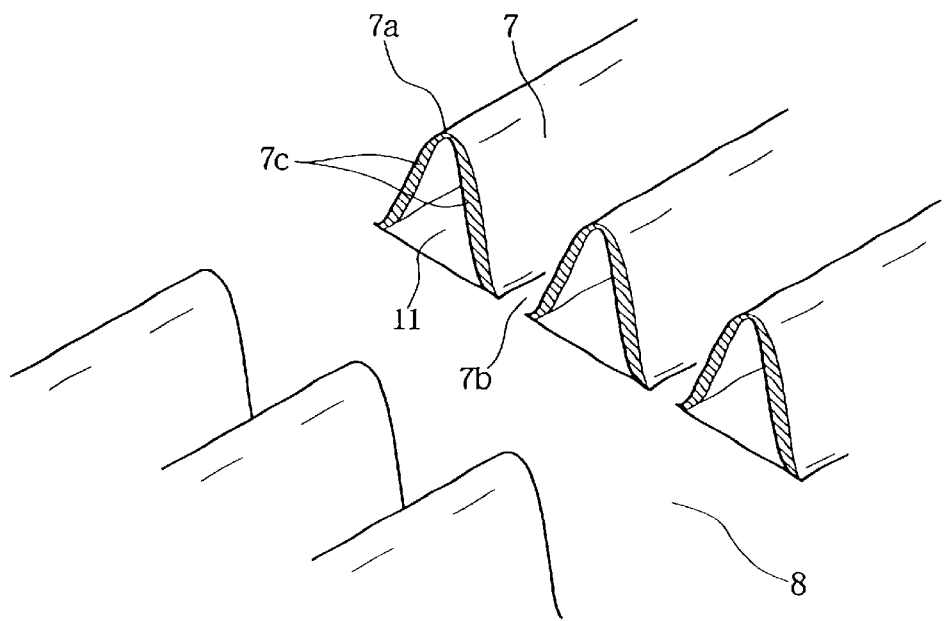
FIG. 9 is an enlarged perspective view of a portion of the side wall sheet which is provided with corrugations, flat portion and holes.

By thus using the shaping rolls 21 and 22 shown in FIG. 6, it is possible to form the corrugations 7, the flat portion 8 and the holes 11 simultaneously. FIG. 9 shows the holes 11 formed by the nonwoven fabric ruptures, in an enlarged scale.

Here, in order to form the holes 11 by causing the ruptures in the nonwoven fabric, the rising angle θ at the two widthwise side portions of the recessed circumference 28 is preferably at least 90 degrees and at most 135 degrees.

In the aforementioned corrugations 7, the fiber density is higher at the ridges 7a and the valleys 7b and lower at the side walls 7c. Therefore, the corrugations 7 have cushioning properties. In the side wall sheets 6 forming the leakage preventing side walls 5, as shown in FIG. 2, the ridges 7a and the valleys 7b are extended from the root ends 5b and 5d to the free end 5c so that the menstrual blood having entered the space between the inner and outer sheet portions 6a and 6b from the holes 11 is guided to the root ends along the higher density portions of the ridges 7a and the valleys 7b.

The density of the higher density portions of the ridges 7a and the valleys 7b is preferably at about 0.1 g/cm³. On the other hand, the opening area of one hole 11 is preferably no less than 0.0012 cm². The menstrual blood easily infiltrates into the leakage preventing side walls 5 from the holes 11, if the opening area of the hole 11 is equal to or more than the above-specified value.

Here, if the confronting inner faces of the inner and outer sheet portions 6a and 6b forming the leakage preventing side wall 5, as shown in FIG. 2, are made water-repellent, the menstrual blood having entered the space between the inner and outer sheet portions 6a and 6b is promptly guided to the root end sides. The water-repellent treatment may be made either by applying a water-repellent hot-melt agent to the inner faces of the inner and outer sheet portions 6a and 6b or by laminating the inner sides of the inner and outer sheet portions 6a and 6b with a water-repellent film.

The array pitch β1, as shown in FIG. 8A, i.e., the pitch of the corrugations 7 is preferable for improving the contact feel on the skin of the wearer, if it is about 0.5 to 1 mm. On the other hand, the rising size from the root end 5b to the free end 5c of the leakage preventing side walls 5 is preferably within a range of 5 to 25 mm.

The elastic member 9 to be attached to the free end 5c of the leakage preventing side wall 5 can be made of natural rubber, synthetic rubber, polyurethane or a styrene-butadiene copolymer and can take a shape of string, filament, film, band (or belt) or the like. Alternatively, the elastic member 9 can be cut from a stretchable nonwoven fabric such as an elastic spun-bonded nonwoven fabric or an elastic melt-blown nonwoven fabric.

The paired side wall sheets 6 provided with the elastic member 9 are jointed to the sanitary napkin 1 while being elongated by about 1.2 to 1.8 times.

The support sheet 2 is preferably made of a liquid-impermeable sheet. This support sheet 2 may be exemplified by an air-permeable resin film, a spun-bonded or spun-laced nonwoven fabric made water-repellent, or a nonwoven fabric having an air-permeable resin film bonded to the back face. Here, the support sheet 2 is preferably provided on its back face with both an adhesive layer to be retained on an external wear such as an underwear and a release sheet for protecting the adhesive layer before the sanitary napkin is used.

The liquid-permeable sheet 4 is made of a nonwoven fabric of PE, PP or PET fibers made hydrophilic or their composite fibers, such as a spun-bonded nonwoven fabric or a spun-laced nonwoven fabric. Alternatively, the liquid-permeable sheet 4 is a resin sheet subjected to an opening treatment.

The liquid absorbing layer 3 is made of pulverized pulp or a mixture of pulverized pulp and a highly water-absorbing polymer, and is prepared by enveloping the pulverized pulp or the mixture of the pulverized pulp and the highly water-absorbing polymer by an absorbent sheet such as tissue paper.

Figure 3:
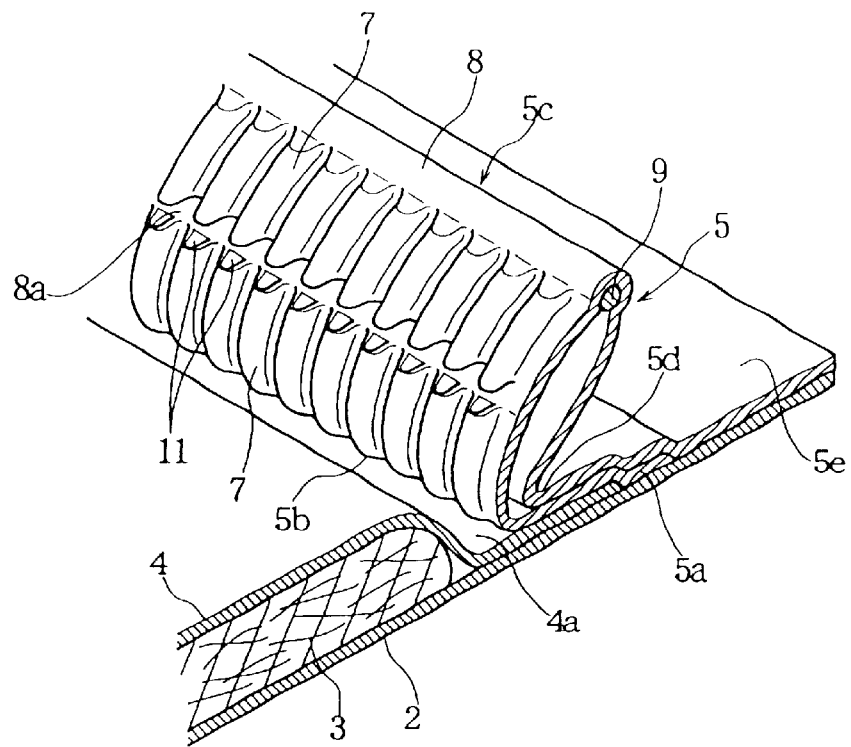
FIG. 3 is a perspective view showing a modification of the sanitary napkin shown in FIG. 2 and including a section.
Figure 4:
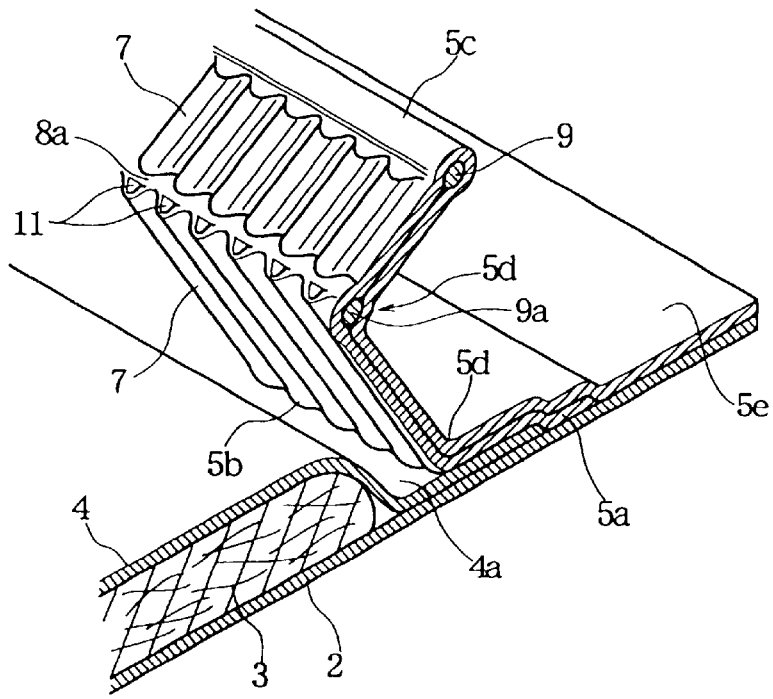
FIG. 4 is a perspective view showing a modification of the sanitary napkin shown in FIG. 3 and including a section.

FIGS. 3 and 4 show modifications of the sanitary napkin shown in FIG. 2.

In the modification shown in FIG. 3, the inner sheet portion 6a of the side wall sheet 6 is formed with a flat portion 8a, midway between the root end 5b and the free end 5c, which extends in the longitudinal direction, and the holes 11 are formed in the boundary portions between the flat portion 8a and the upper and lower corrugations 7. In this case, the holes 11 are preferably formed in the root end 5b, too, and may also be formed in the free end 5c as in FIG. 2.

FIG. 4 shows a modification of the sanitary napkin shown in FIG. 3. In this modification shown in FIG. 4, as in FIG. 3, the flat portion 8a is formed midway between the root end 5b and the free end 5c, and the holes 11 are formed in the boundary portions between the flat portion 8a and the upper and lower corrugations 7. Moreover, an elastic member 9a is jointed to the inner side of the flat portion 8a. The leakage preventing side wall 5 is so folded into the shape of letter "L" across that flat portion 8a that the folded portion from the flat portion 8a to the free end 5c is directed to the widthwise outer side. In this case, too, the holes 11 may be formed in the root end 5b and/or the free end 5c.

In FIGS. 3 and 4, the menstrual blood easily infiltrates, when it blots the surface of the inner sheet portion 6a of the side wall sheet 6, into the leakage preventing side wall 5 from the holes 11 opened in the midway portion.

Here in the embodiments shown in FIGS. 2 to 4, the single side wall sheet 6 is folded back at the free end 5c so that the leakage preventing side wall 5 is formed of the two folded portions (i.e., inner and outer sheet portions) of the single side wall sheet 6. However, the leakage preventing side wall 5 may also be formed of two or more side wall sheets by jointing them one another. For example, a side wall sheet raised from the root end 5b and another side wall sheet raised from the root end 5d can be jointed at the free end 5c or at another region to form a jointed portion extending in the longitudinal direction (or the direction Y).

In the leakage preventing side wall 5, the outer sheet portion 6b may be formed with the corrugations 7 like the inner sheet portion 6a, or may not be corrugated. Here, it is preferable that the holes 11 are not formed in the outer sheet portion 6b.

The holes 11 may be formed not by rupturing the nonwoven fabric but by opening the same by the pin-pressing method.

Although the invention has been described on the embodiment in which the absorbent article is embodied by the sanitary napkin, it can also be applied to a disposable diaper, a urine absorbing pad or another absorbent article.

According to the invention, as has been described in detail hereinbefore, the liquid having blotted the leakage preventing side walls is guided thereinto so that it is not left on the surfaces of the leakage preventing side walls. Therefore, the sideway leakage can be prevented and the contact feel of the skin of the wearer-with the leakage preventing side walls can be improved.

Here, 'comprises/comprising' when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:

a main body including a support sheet, a liquid absorbing layer laid on said support sheet, and a liquid permeable sheet provided on a liquid receiving surface of the main body and covering said liquid absorbing layer; and leakage preventing side walls provided on said main body, the leakage preventing side walls lying opposite one another in a transverse direction of the absorbent article and extending in a longitudinal direction of the absorbent article, each leakage preventing side wall having a root end jointed to the liquid receiving surface of the main body and a free end positioned away from the liquid receiving surface of the main body, wherein each leakage preventing side wall has a non corrugated portion and a corrugated portion having ridges and valleys, which extend from the root end to the free end and alternate with each other in the longitudinal direction, and wherein along a longitudinally extending boundary between the non corrugated portion and the corrugated portion, ends of the individual ridges are ruptured and separated from the non corrugated portion to thereby form holes leading to a space inside the leakage preventing side wall.

* * * * *